United States Patent [19]
Drobish et al.

[11] Patent Number: 5,639,658
[45] Date of Patent: Jun. 17, 1997

[54] SPLIT FEED CELL FERMENTATION SYSTEM

[75] Inventors: Kenneth Mitchell Drobish, Thousand Oaks; Vasuki Nagaraju Satyagal, Newbury Park; Raj Kumar Sachdev, Camarillo, all of Calif.

[73] Assignee: Amgen Inc., Thousand Oaks, Calif.

[21] Appl. No.: 347,784

[22] Filed: Nov. 30, 1994

[51] Int. Cl.$^6$ ............................................. C12N 1/00
[52] U.S. Cl. ......................... 435/243; 435/248; 435/252.1
[58] Field of Search ............................ 435/243, 286.5, 435/289.1, 248, 249, 252.1, 252.8

[56] References Cited
FOREIGN PATENT DOCUMENTS
290215 A5   7/1988   Germany ........................ C12N 1/20

OTHER PUBLICATIONS

Jung et al., High–Cell Density Fermentation Studies of Recombinant *E. coli* Strains Expressing Human Interleukin–1 β, *ICSU Short Rep 8 Miami Bio/Technol Winter Symp.*, p. 60 (1988).

Tsai et al., The effect of organic nitrogen and glucose on the production of recombinant human insulin–like growth in high cell density *Escherichia coli* fermantations, *J. of Industrial Microbiology*, 2 (1987) pp. 181–187.

*Primary Examiner*—David A. Redding
*Attorney, Agent, or Firm*—Nancy A. Oleski; Ron Levy; Steven M. Odre

[57]   ABSTRACT

Provided are methods for fed batch fermentation of cells to produce a compound of interest. Also provided are methods of preparing a compound of interest.

7 Claims, 2 Drawing Sheets

SPLIT FEED CELL FERMENTATION SYSTEM

BACKGROUND

1. Field of the Invention

This invention relates to a split feed fed batch fermentation system for culturing submerged host cells that produce a compound of interest. More specifically, the invention concerns a method whereby organic carbon and nitrogen nutrient sources for the cultured cells are maintained as separate media solutions and are fed independently into a fermentor containing cultured host cells.

2. Description of the Related Art

Production of Pharmaceutical Compounds of Interest

Compounds of interest to the pharmaceutical industry such as certain organic compounds, proteins and carbohydrates, can be produced in large quantities by culturing cells (typically referred to as "host cells") in a liquid nutrient solution. These host cells have either been engineered to produce such compounds, or they produce the compounds naturally. Typically, the host cells are submerged in a tank (often referred to as a "fermentor") containing a liquid nutrient solution (medium) for a set period of time. During culturing or fermentation, the cells grow, multiply, and synthesize the compound of interest. The compound can then be collected either from the culture medium, or by harvesting the cells and extracting the compound directly from the cells.

Many different species and strains of host cells, either aerobes or anaerobes, can be used for preparation of compounds of interest. Selection of the host cell species is usually dependent on the nature of the compound to be produced. For example, heavily glycosylated recombinant proteins are typically produced in eukaryotic host cells. A commonly used eukaryotic cell line is a Chinese hamster ovary cell line (CHO cell line). Yeast or fungal cells such as Streptomyces are useful hosts for making certain recombinant polypeptides that are lightly glycosylated, as yields of the polypeptide from yeast cells can be greater than yields from mammalian cells. Bacterial cells such as *E. coli* or Bacillus are often preferred for manufacturing non-glycosylated polypeptides. Bacterial cells are generally considered to be the easiest cell type to culture, as their nutritional requirements are relatively simple, their growth rate is higher, and they can be grown to relatively high densities in a fermentor as compared to eukaryotic cells.

Commercial-scale fermentation has been used successfully to prepare several human recombinant polypeptide pharmaceutical compounds such as, for example, insulin, erythropoietin, granulocyte-colony stimulating factor (G-CSF), tissue plasminogen activator (t-PA), and human growth hormone (hGH), as well as many other polypeptides.

Fermentation Systems

A variety of fermentors and fermentation systems exist for submerged culturing of cells, and selection of a suitable fermentation system is dependent on a number of factors such as, for example, the amount of the compound to be produced, the host cell species to be employed, whether the compound is secreted by the host cells, the duration of fermentation, and the resources and capital available.

Two commonly used fermentation systems are the continuous culture system and the fed batch culture system. The continuous culture system is typically used to extend the growth phase of the cultured cells over long periods of time by providing fresh medium to the cells while simultaneously removing spent medium and cells from the fermentor. Such a culturing system serves to maintain optimal culturing conditions for certain cell types and products, i.e., constant volume of medium in the fermentor, constant cell concentration in the fermentor, and constant product concentration in the fermentor. Steady-state maintenance of cell density is accomplished by providing sufficient levels of all required nutrients to the cells.

Fed batch fermentation systems are generally defined as batch culture systems wherein fresh nutrients and/or other additives (such as precursors to products) are added but no medium is withdrawn. In one type of fed batch fermentation system, the fermentation period is divided into two phases, a growth phase, and a production (or synthesis) phase. The growth phase, which commences upon introduction (inoculation) of the host cells into the fermentor, is the time period during which the host cells grow and divide, thereby increasing the host cell density. The length of this phase is primarily a function of the type of host cells being cultured and the rate at which they multiply. After the host cells have achieved the desired density in the fermentor, the fermentation conditions can be altered such that the host cells are induced to produce the compound of interest (the production or synthesis phase).

This type of fed batch fermentation system is often appropriate for cells that can produce a compound in a manner that is decoupled from their growth, as is the case for many polypeptides produced using recombinant DNA technology. For example, production of many heterologous polypeptides in bacterial host cells is typically independent from the growth of the cells. In these cells, the maximum amount of product is often produced by growing the cells to a certain density, and then inducing the cells (by addition or removal of certain compounds or by changing the temperature of the culture medium, for example) to synthesize large quantities of polypeptide. Once the amount of the compound produced by the cells levels off, the cells, medium, or both can be harvested to obtain the compound of interest.

The fermentors used in fed batch culture systems often have probes attached. The probes can monitor various parameters during the fermentation process. The probes may be attached to a computer. Such parameters as dissolved oxygen, optical density, respiratory quotients, pH, temperature, and the concentration of such toxic compounds produced by the host cells such as acetate can be monitored either directly by the probes, or by removing samples of the culture medium and analyzing them off-line using standard assays. By monitoring these parameters, the optimal time to change the medium from the growth medium to the production medium can readily be identified.

The selection of the growth phase and production phase media to be used in a fed batch culturing system is primarily a function of the nutritional requirements of the host cell line used, the rate of growth of the cells, and the chemical composition of the compound to be produced. Often, the organic nitrogen content of the medium will be different for growth phase and production phase media, especially where the compound to be produced is a protein. For example, Tsai et al. (*J. Indust. Microbiol.*, 2:181–187 [1987]) cultured *E. coli* cells engineered to produce the polypeptide IGF-1 in a fed batch culture system. They found that the yield of IGF-1 increased if the amount of organic nitrogen was increased in the production phase medium. Jung et al. (*Miami Bio/Technol. Winter Symp.*, 8:60 [1988]) found that an increased level of yeast extract (a standard source of organic nitrogen) in the medium added to the *E. coli* host cells during the production phase resulted in an increased production level of the polypeptide IL-1 beta by the cells.

Certain problems with the preparation of fermentation media have been routinely encountered. For example, it is believed that some sugars or carbohydrates can form covalent complexes with organic phosphate groups during heat sterilization. Thus, these two components of many media are not generally heat sterilized together. Instead, it is generally preferred to sterilize them in separate solutions, and then recombine them at a lower temperature to form the completed medium.

Another problem commonly encountered in preparing fermentation media is the formation of precipitates either before, during, or after sterilization, which can be due to over saturation of the solutions.

Producing biological compounds by fermentation, especially fed batch fermentation, is an expensive procedure, as the demand for purified water and clean steam (for sterilization) can be high, the process is generally labor intensive, requiring skilled workers at all levels of production, and the cost of high grade nutrients and other ingredients necessary for culture media can be high.

There is thus a need in the art to provide a simple fed batch fermentation system that minimizes the cost for production of a compound of interest such as a polypeptide by 1) reducing the number of tanks and sterile media transfers necessary for the fermentation process; 2) providing required nutrients to cells in a more timely and cost effective manner so as to minimize cost and maximize yield of the compound of interest; and 3) reducing problems that may occur in media preparation such as precipitation of certain ingredients or the formation of chemical intermediates during sterilization.

Accordingly, it is an object of the present invention to provide a fermentation system that reduces the cost of production of biological compounds, decreases the number of tanks to be sterilized, and provides nutrients to the cultured cells in a more cost efficient manner as compared with known methods.

SUMMARY OF THE INVENTION

In one embodiment of the present invention a method for fed batch culturing of cells in a fermentor is provided comprising independently introducing into the fermentor: a carbon nutrient source from a first feed vessel and a nitrogen nutrient source from a second feed vessel.

In another embodiment, the carbon and nitrogen nutrient sources are independently introduced into the fermentor by a rate control means; the rate control means can be a pump or a valve which can be operated manually or by computer.

In yet another embodiment, the cultured cells are bacteria cells, and optionally are *E. coli* cells.

In one other embodiment, a fed batch cell culture system is provided comprising a fermentor and at least a first and a second feed vessel, wherein the vessels are operably connected to the fermentor, and wherein the first feed vessel delivers a carbon nutrient solution and the second feed vessel delivers a nitrogen nutrient solution; the nutrient solutions are delivered to the fermentor independently by a rate control means.

In still another embodiment, a method for preparing a compound of interest is provided comprising fed batch culturing of host cells that produce the compound in a fermentor, wherein a carbon nutrient source is introduced to the fermentor from a first feed vessel and a nitrogen nutrient source is introduced to the fermentor from a second feed vessel. In this method, the carbon and nitrogen nutrient sources are independently introduced to the fermentor by a rate control means.

DETAILED DESCRIPTION OF THE INVENTION

Figure 1:
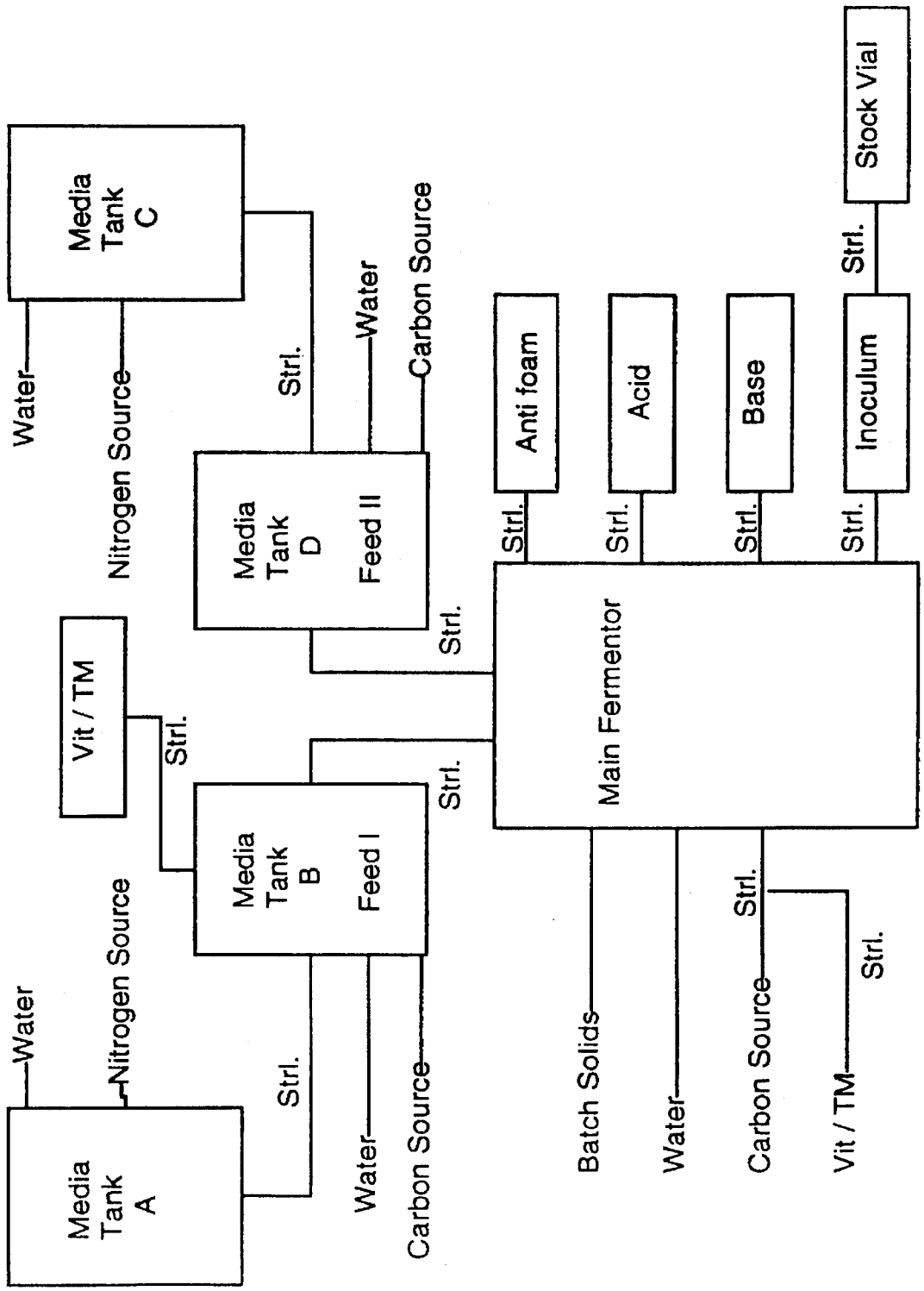
FIG. 1 depicts a fed batch fermentation system such as that used by Tsai et al., supra, for culturing host cells that produce a biological compound of interest. The four media tanks used are indicated as Tanks A, B, C, and D. "VIT/TM" refers to vitamins and trace metals; "STRL." refers to sterile transfer; "FS" refers to filter-sterilized.

The present invention is based on the discovery that media preparation and delivery of the media to host cells cultured in a fed batch fermentation system can be simplified by maintaining the media as two or more separate and distinct formulations. These media are kept in separate feed vessels and are delivered to the fermentor independently, i.e., either at the same rate or disproportionally during fermentation; the rate of delivery of each solution can vary over the fermentation period. Where the host cells are engineered to produce a recombinant polypeptide, one media formulation will usually contain a high concentration of glucose or another organic carbon source (other simple sugars such as fructose, sucrose, sorbitol, maltose, or lactose; and/or a starch or complex carbohydrate), and will typically be utilized in a higher proportion during the growth phase of host cell fermentation. A second media formulation will typically contain a relatively high concentration of an organic nitrogen source such as yeast extract, trypticase peptone, and/or a protein hydrolysate, and will usually be utilized at a higher proportion during the production phase of host cell fermentation. Such a fermentation system wherein the organic nitrogen and carbon nutrient solutions are maintained separately, requiring in many cases only two media tanks, provides a simplified means for fermentation as compared with known fermentation systems such as the one described by Tsai et al., supra. The fed batch fermentation system described by these investigators requires the use of four separately sterilized feed vessels during fed batch fermentation of *E. coli* cells that produce recombinant IGF-1. Two sterilized vessels contain glucose nutrient solutions (each at a different concentration), and two sterilized vessels contain organic nitrogen nutrient solutions (each at a different concentration). One part of glucose solution is then mixed with one part of nitrogen solution after sterilization.

In the present invention, the problem of precipitation of certain nutrient components in a complex medium can be reduced or eliminated in many cases, as the salts believed to be responsible for inducing precipitation, for example magnesium sulfate and potassium phosphate, may be separated between two or more feed tanks. The precipitation problem is further avoided by preventing over-saturation of any one solution by separating the organic nitrogen and carbon sources from each other. In addition, delivery to the fermentor of selected nutrients at particular concentrations during set times of the fermentation period is made possible by the present invention. Selected nutrient delivery can reduce the costs and time associated with preparation and supply of nutrients to the cells.

The fermentation systems and methods of the present invention generally are useful for the submerged culturing of free-floating individual prokaryotic cells or groups or clumps of these cells, or cells immobilized by attachment to beads or other component, whether the cells are aerobic or anaerobic. The methods provided herein are generally applicable to all types of fermentation systems, but are particularly well suited to fed batch fermentation systems, where the host cells are induced after growth to produce a compound of interest.

Any species and strain of cell may be cultured using the fed batch fermentation systems and methods of the present invention, whether anaerobe or aerobe, and including, without limitation, plant cells, bacteria and other prokaryotic cells, yeast and fungal cells, invertebrate cells, and vertebrate cells. Preferred host cells are yeast, fungal, prokaryote, and certain mammalian cells. More preferred host cells are strains of E. coli, Bacillus, Pseudomonas, Streptomyces, Saccharomyces, Cornybacteria, Aspergillus, Xymonas, Xanthomonas, as well as Chinese hamster ovary cells and COS-7 cells.

The fermentation methods and systems described herein are suitable for compound a wide variety of compounds of interest. A number of compounds produced naturally by various cells are amenable to production herein such as antibiotics, including without limitation, penicillin and related compounds, ampicillin, erythromycin, tetracycline, cephalosporins and related compounds, and rhodomycin; feed additives or animal antibiotics such as tylosin; and simple sugars and carbohydrates, including without limitation, aminoglycosides such as tobramycin, gentamycin, and kanamycin. As one of ordinary skill in the art will appreciate, the exact composition of the batch, growth, and production media will vary by host species and by compound of interest to be produced.

In addition to methods and systems for production of naturally occurring compounds, the methods and systems of the present invention can be used for fermentation of host cells that have been genetically engineered to either produce compounds that they do not naturally synthesize, or to produce compounds that they naturally make but only at a very low level. Genetic engineering will typically require that the host cell be modified with a suitable DNA construct which encodes one or more polypeptides and some regulatory elements as well, to enable it to produce the polypeptides. The polypeptide(s) encoded by the DNA may be the compound of interest itself, or it may be an enzyme(s) that is used by the host cell to synthesize the compound of interest The components of the DNA construct used for such genetic modification of a host cell will depend on the host cell used. For most host cells, a plasmid vector will typically be used to transfect the cells. The plasmid vector will normally contain the gene(s) encoding the biological compound of interest; such gene(s) may also contain a signal sequence which is usually linked to the 5' end of the gene encoding the biological compound and can serve to secrete the compound from the cell. The gene(s) with or without a signal peptide sequence attached will be operably linked to a promoter that can regulate expression of the gene(s). The selected promoter may be homologous or heterologous, and may be constitutive or inducible. Suitable promoters for bacteria include, for example, $T_5$, $T_7$, $P_R$, $P_L$, lac, tac, trp, and tna.

Other components of such plasmids may include, without limitation, an origin of replication sequence (ori), an antibiotic resistance gene (such as tetracycline or ampicillin) or other selectable marker gene, an enhancer element(s), a polylinker region, and a polyA sequence. One of ordinary skill in the art will recognize which of these components must be used in a given host cell. One of ordinary skill in the art will further recognize how to place these components on a vector in a particular manner so as to render them functional (i.e., the promoter is typically located 5' to the gene encoding the polypeptide; the polyA sequence is typically just 3' to the gene encoding the polypeptide). The plasmid vector may be transfected into the host cell using a variety of well known methods such as calcium chloride transfection, electroporation, microinjection, and the like.

As one of ordinary skill in the art will readily appreciate, the precise ingredients of each culture medium used for fermentation of the host cells will vary between and among cell species and strains, as the nutritional requirements of cells vary.

The cells cultured in the fermentor systems of the present invention may produce a compound of interest either constitutively or by induction. Where the compound is produced by the cells upon induction, induction may be by any suitable means such as by increasing or decreasing the temperature of the medium in which the cells are fermented, and/or by addition or subtraction of a chemical or chemicals used either to affect the rate of expression of one or more genes or promoters, or as a precursor for production of the compound of interest. The sterile induction solution or compound may be added at the appropriate time to one of the feed vessels. In this way, it will be added to the fermentor simultaneously with the carbon or nitrogen media formulation at a particular time period during the fermentation period. Alternatively, the sterile induction solution or compound may be placed in its own feed vessel; this vessel would then be operably connected to the fermentor at the appropriate time during the fermentation period. Still another alternative may be to add the sterile induction solution or compound directly to the fermentor.

By way of example, production of a polypeptide of interest in a bacterial cell may be induced by addition of lactose to the culture medium where the gene encoding the protein is operably linked to a promoter that is positively regulated by lactose. To induce production of the polypeptide, the lactose can be added directly to the fermentor, or to one of the feed vessels.

The apparatus of the present fermentation system (also referred to as a cell culture system) may contain several elements. Independent of the configuration employed, the fermentation systems of this invention all comprise a fermentor (also referred to as a culturing vessel, culturing tank, reactor, or bioreactor) operably connected to at least two feed vessels (also referred to as media tanks). As used herein, the term "operably connected" refers to a physical connection, or "feed line", between the fermentor and the feed vessels such that a nutrient or other solution can flow from the feed vessel to the fermentor. Typically, the feed line used to operably connect the fermentor to the feed vessels is comprised of tubing or steel piping.

The fermentor contains the cultured cells submerged in a liquid nutrient medium. As such, the fermentor usually is equipped with a means to oxygenate the cells in solution, unless the cells being cultured are anaerobes. Typical means to oxygenate the tank include a stirring mechanism which is often part of the fermentor itself (commonly termed a stirred tank reactor or STR) or an inlet wherein oxygen is pumped into the fermentor. Other such means include, for example, "air lift" fermentors, or oxygenation of the feed vessels which feed into either a packed bed or a fluidized bed fermentor.

Aside from a means to aerate the cultured cells, other useful components contained on fermentors used in the present invention include, without limitation, probes for pH, dissolved oxygen, and temperature measurements, a pressure sensor (for those fermentors that can be sterilized in situ) as well as one or more ports for addition of nutrient and/or other solutions such as antifoam from the feed vessels.

The fermentor and feed vessels may be of any size and constructed of any material that is amenable to sterilization and is inert with respect to the nutrient solution(s) and/or cells to be placed in them. Preferred fermentors and feed vessels will have an airtight seal for ease of in situ sterilization. One preferred material for construction of the fermentor and the feed vessels is stainless steel.

The feed lines used to operably connect the fermentor to each feed vessel may be made of any material that can be sterilized and is inert with respect to the nutrient and/or other solutions that pass through the feed lines. For very large scale fermentors (on the order of 1,000 liters or more), stainless steel piping is often the material of choice because it is durable under pressure and is amenable to steam sterilization. For smaller scale systems, autoclavable tubing made of silicone, rubber, or plastic for example, is often preferred due to its ease of manipulation.

The rate, timing, and volume of delivery of the nutrient (or other) solution from each feed vessel to the fermentor through the feed lines is typically varied over the course of fermentation. Adjustment of the flow rate of each solution from each feed vessel can be set using a variety of techniques, or "rate control means", such as for example, by attaching a peristaltic or other suitable type of pump such as a diaphragm-dosing pump to each feed line; the pump may be regulated manually or by computer. Alternatively, the flow can be regulated by establishing a pressure gradient between each feed vessel and the fermentor. These systems can be controlled through the use of valves attached to the inlet(s) to the fermentor and/or valves attached to the outlet of each feed vessel. The valves may be actuated by mechanical or electronic means (such as by computer), or, where appropriate, manually.

Each feed vessel may be connected directly to the fermentor via a separate feed line, or the feed line from each vessel may be connected directly to a main feed line, which in turn is connected to the fermentor.

The fermentation apparatus may be assembled in any configuration that is suitable taking into account physical space limitations in the laboratory or production plant. In some cases, it may be desirable to keep the feed vessels in a separate room from the fermentor in order to avoid potential contamination and/or sterility problems.

The fermentation process is generally commenced by adding an inoculum of cells to a starting batch culture medium in a small (i.e., 500 ml to 3 liter) flask. The cells are usually grown up to a desired density and the contents of the flask are then transferred to the fermentor (containing a starting batch culture medium as discussed below) under sterile conditions. For bacteria such as *E. coli* cells, a standard medium such as LB (Luria Bertani medium; described in Example 2 below) is generally acceptable for use in the flask.

The starting batch culture medium will typically contain all nutrients essential for growth and multiplication of the cells. The batch medium composition will vary by and among species, as amino acid, carbohydrate, vitamin, mineral, and other requirements often differ by species. For example, the batch medium for bacteria cells such as *E. coli* will typically be composed of an organic nitrogen source such as trypticase peptone, yeast extract, sodium chloride, glucose or other organic carbohydrate, magnesium sulfate, potassium phosphate, trace minerals and vitamins. Often, one or more buffering agents will be added as well.

Commonly used batch media for bacterial and other prokaryotic host cells include, for example, Luria-Bertani Medium (LB), YT Medium, Terrific Broth (TB), SOB Medium, or SOC Medium. All of these media contain as their main ingredients Bactotryptone or an equivalent, yeast extract, and sodium chloride; the precise formulation of each is set forth in Miller, J., *A Short Course in Bacterial Genetics* (Cold Spring Harbor Laboratory Press, Cold Spring Harbor, N.Y. [1992]).

For animal cell cultures, commonly used batch culture media include, for example, Eagle's minimal essential medium (MEM), Dulbecco's modified MEM (DMEM), Ham's F12 medium, RPMI 40, and Waymouth's MB 752/1. Many of these media are supplemented with fetal calf or bovine serum, although serum is not always required. In addition, the media may be supplemented with various other growth and/or differentiation (promoting or inhibiting) substances such as hormones, cytokines and the like. The formulations for each of these media are set forth in Atkinson and Mavituna, *Biochemical Engineering and Biotechnology Handbook* (2nd ed., M Stockton Press, Macmillan Publishing Co. [1991]). The type and amount of supplements added to each medium will vary depending on the animal cell culture line used, however the appropriate supplements to be used will readily be apparent to those of ordinary skill in the art.

Commonly used basic batch media for plant cells are MS (Murashige and Skoog) medium, and Gamborg medium; the formulation of each of these is set forth in Atkinson and Mavituna, supra. These media may be modified with hormones and/or other growth promoting substances as is appropriate for the type of cell to be cultured.

The batch medium is typically sterilized either before or after introduction into both the flask (used for initial scale-up of the cell inoculum) and the fermentor. In some cases, certain components of the medium cannot be sterilized together, as chemical intermediates may form between certain components of the medium during heat sterilization, thereby altering the composition of the medium and the concentration of certain nutrients in the medium. In these cases, the medium may be prepared as two or more separate media, wherein known incompatible components are kept separate from one another during sterilization. These separate media can then be combined after sterilization to create the complete, sterile medium. By way of example, it is believed that certain carbon sources such as glucose, when combined and heated with organic phosphate compounds, tend to form covalent intermediate complexes. Therefore, it is preferred to sterilize these two components, which are found in many media, separately and then combine them at a lower temperature.

Additionally, some substances, particularly certain proteins such as hormones or vitamins, are not amenable to heat sterilization, as they may be heat-denatured. Denaturation can be avoided by filter sterilizing these substances before adding it to the medium.

After the batch medium has been inoculated and the cells begin to grow and multiply, certain nutrients may gradually be depleted from the medium. Depletion of growth rate-limiting nutrients can be monitored via probes inserted into the medium that are designed to detect particular nutrient levels, or by removing samples from the medium and analyzing them. Once these nutrient levels fall below an acceptable level, one or more of the feed vessels can be activated to supply the necessary nutrients to the fermentor. Due to the changing nutritional requirements of many cells in a fed batch culture system as they progress from the growth to the production phase, one feed vessel may contain a medium that supplies primarily those nutrients that are thought to be limiting during the growth phase. Such nutrients are host cell type dependent, but typically include, for example, an organic carbon source such as glucose, fructose, sucrose, maltose, lactose, sorbitol, or other simple sugars; oligosaccharides; simple starches; complex carbohydrates; or mixtures of any of these compounds. This feed vessel may be engaged relatively early during the fermentation period, and may be slowed down or completely shut off during the production phase. A separate feed vessel may contain those nutrients that are thought to be primarily essential or beneficial to the host cells during the production phase, such as, for example, an organic nitrogen source, including without limitation, protein hydrolysates of casein, lactalbumin, albumin, soy protein, and/or meat protein; yeast extract; trypticase peptone; or mixtures of individual amino acids. Combinations of any of these organic nitrogen sources may also be appropriate. The choice of an organic nitrogen source will be primarily dependent on the type of host cell being cultured. This feed vessel may thus be engaged just prior to, or at the onset of, the production phase.

An alternative and preferred means to supply the various required nutrients at suitable levels to the host cells during the two phases is to simultaneously feed both nutrient solutions to the fermentor during certain phases of the fermentation period, but at independent flow rates. In this way, the concentration of individual nutrients may be selectively altered during fermentation such that they are supplied in large quantities when needed, and smaller quantities when the demand for them decreases. Using this approach, nutrients are conserved, and the process of supplying the optimal concentration of nutrients in a timely manner is simplified.

After the fermentation of the host cells is completed, the compound of interest may be obtained from the culture medium, from the host cells, or both. If the compound of interest has been secreted by the host cells into the culture medium, the medium may be collected, and the compound purified from it. Purification typically involves a number of steps, and these steps will vary depending on the nature of the biological compound. Such techniques as dialysis, molecular sieve chromatography, ion exchange chromatography, affinity chromatography (using an antibody or enzyme substrate analog, for example as the affinity matrix), ammonium sulfate precipitation, immunoprecipitation, and/or HPLC can be used for purification of the compound of interest from the culture medium. Typically, several of these techniques will be employed in a series of steps to successively increase the purity of the compound.

The compound of interest may need to be treated after purification to gain activity. For example, polypeptides often require "refolding", or conformational assembly to be active. Refolding may consist of exposing the polypeptides to certain pH conditions and/or to certain other renaturing or chaotropic agents such as guanidine or urea. The steps required for such treatment will readily be known to one of ordinary skill in the art.

Where the compound of interest remains in the host cells or, in the case of gram negative bacteria, in the periplasm in the form of inclusion bodies, a number of different techniques can be used to extract the compound from the cells and purify it. For extraction of the compound from the host cells, the host cells are usually first collected, as for example, by pelleting in a centrifuge and then lysed using an enzyme solution and/or a detergent, or by pressurizing them or sonicating them. Cellular material (such as membranes, cell wall material, and the like) can then be separated by additional centrifugation. In the case of gram negative bacteria host cells, this pellet will usually contain the inclusion bodies. This material can be treated with a chaotropic agent such as urea to release and break apart the inclusion bodies and to solubilize the polypeptide. For host cells without inclusion bodies, the compound of interest will generally be found in the supernatant. The compound of interest, now in a soluble form, can be purified using techniques such as those described above.

The invention can be more fully understood by reference to the following examples. These examples are intended for illustrative purposes only, and should not be construed in any way as limiting the scope of the invention.

EXAMPLES

Example 1

Production of SCF Using Conventional Fed-Batch Fermentation

The procedure employed to prepare recombinant human stem cell factor (rSCF) is readily understood by reference to FIG. 1.

About 5.3 liters of batch medium used in the fermentor for initial growth of the host cells was prepared by adding to the fermentor about 10.0 g/l of yeast extract (Becton-Dickinson, Cockeysville, Md.), NaCl to a final concentration of about 0.625 g/l, and monobasic potassium phosphate and dibasic potassium phosphate at about 4.0 g/l each. Antifoam (Dow P-2000, Dow Chemical Company) was then added at a concentration of about 1 g/l initially, and then subsequently as needed to prevent foaming. The solution was heat sterilized in situ. About 200 ml of a solution containing about 40 g glucose and a solution of vitamins and trace metals (including biotin, folic acid, riboflavin, pyridoxine, niacin, pantothenic acid, iron, zinc, cobalt, molybdate, calcium, copper, boron, and manganese), as well as a solution of 1M magnesium sulfate ($MgSO_4*7H2O$), each of which had been previously sterilized, were then added to the fermentor through a port, bringing the final glucose concentration to about 5 g/l, and the final magnesium sulfate concentration to about 4 ml/l. Acid and base solutions of ammonium hydroxide and phosphoric acid were added as necessary to maintain a pH of about 7.0.

A vial of previously frozen E. coli cells strain K-12 that had been transfected with a plasmid containing the gene encoding human SCF (PCT patent application WO 91/05795, published 2 May 1991) was slowly thawed and added under sterile conditions to an inoculum shaker flask containing about 500 ml LB broth. The flask was kept shaking at about 30° C. After about 8–12 hours (or when the $OD_{600}$ was greater than 1.0), the shaker flask of cells was transferred under sterile conditions to a fermentor. The fermentor was sparged with air and oxygen as needed.

When the $OD_{600}$ reached about 5.0 (indicating that the glucose level was less than about 0.5 g/l), Feed 1, which was attached to the fermentor by silicone tubing, was started. The contents of Feed 1 were prepared as follows.

About 167 g/l of yeast extract (Becton-Dickinson, Cockeysville, Md.) and about 43 g/l of $K_2HPO_4$, both in the solid form, were added to a vessel and brought to about 3 liters with distilled water. This solution was then heat sterilized and then transferred to a media tank (Media Tank A in FIG. 1). About 6.5 liters of a second media solution was prepared containing glucose at about 642 g/l; about 50 ml/l of a solution of 1M $MgSO_4*7H_2O$ in distilled water was then added. This second media solution was heat sterilized in a vessel and then transferred to a media tank (Media Tank B in FIG. 1). After sterilization, a solution of trace metals and vitamins was added to Media Tank B. Media Tank A was then sterilly transferred to Media Tank B, which in turn was connected to the fermentor by silicone tubing. Feed 1 was then pumped into the fermentor via a peristaltic pump. The flow rate of Feed 1 was gradually increased over time, as shown in Table 1 below.

TABLE 1

VOLUMETRIC AND MASS FLOW OF FEED 1

| TIME (hrs) | VOLUMETRIC FLOW (ml/hr) | MASS FLOW (g Glucose/hr) |
|---|---|---|
| 0.00 | 16.50 | 7.43 |
| 2.00 | 27.40 | 12.33 |
| 4.00 | 45.20 | 20.34 |
| 6.00 | 74.60 | 33.57 |
| 8.00 | 123.00 | 55.35 |
| 9.00 | 158.00 | 71.10 |
| 10.00 | 203.00 | 91.35 |
| 11.11 | 270.00 | 121.50 |

After about 10 hours, or when the $OD_{600}$ reached about 50, the host cells were induced to produce SCF by increasing the temperature of the fermentor to about 42° C. Feed 2 was started simultaneously with increasing the fermentor temperature, and Feed 1 was stopped. As for Feed 1, Feed 2 was prepared as two separate media that were then combined for delivery to the fermentor. The first of these media, Media C, was prepared by adding about 250 g/l of Trypticase Peptone (Becton-Dickinson, Cockeysville, Md.), about 125 g/l of yeast extract, and about 8 g/l of $K_2HPO_4$, all in a solid powder form, to Media Tank C. Distilled water was then added to about 8 liters, and the solution was then heat sterilized. Media Tank D was prepared by adding about 750 g/l glucose to about 2 liters of distilled water. This solution was then heat sterilized. Media Tank C was then sterilly transferred to Media Tank D, which was connected to the fermentor via silicone tubing. The flow of Feed 2 was regulated by a peristaltic pump. The flow rate of Feed 2 was maintained at about 225 ml/hr.

The composition of the media added to the fermentor from Feed 2 during the rSCF production phase is shown below in Table 2.

TABLE 2

| BACTO TRYPTONE (g/hr) | 45 |
|---|---|
| YEAST EXTRACT (g/hr) | 22.5 |
| K2HPO4 (g/hr) | 1.46 |
| GLUCOSE (g/hr) | 33.75 |
| MGSO4*7H2O (ml/hr) | 0 |
| TM (ml/hr) | 0 |
| VITAMINS (ml/hr) | 0 |

After about 10 hours, the fermentation process was terminated by chilling the fermentor to about 10° C. The rSCF was collected by harvesting the cells, extracting the inclusion bodies, and purifying the rSCF from the inclusion bodies.

The yield of rSCF, as estimated from SDS-polyacrylamide gel electrophoresis for each of five separate fermentation runs, is set forth below in Table 3. Yield is calculated as grams of rSCF per liter of fermentation broth.

TABLE 3

YIELD OF rSCF

| Run No. | Final $OD_{600}$ | rSCF Yield (g/l) |
|---|---|---|
| 1 | 62 | 2.14 |
| 2 | 61 | 1.65 |
| 3 | 61 | 2.43 |
| 4 | 65 | 2.54 |
| 5 | 59 | 2.04 |
| Average | 62 | 2.16 |

Example 2

Production of rSCF Using a Split Feed Fed Batch Fermentation System

Figure 2:
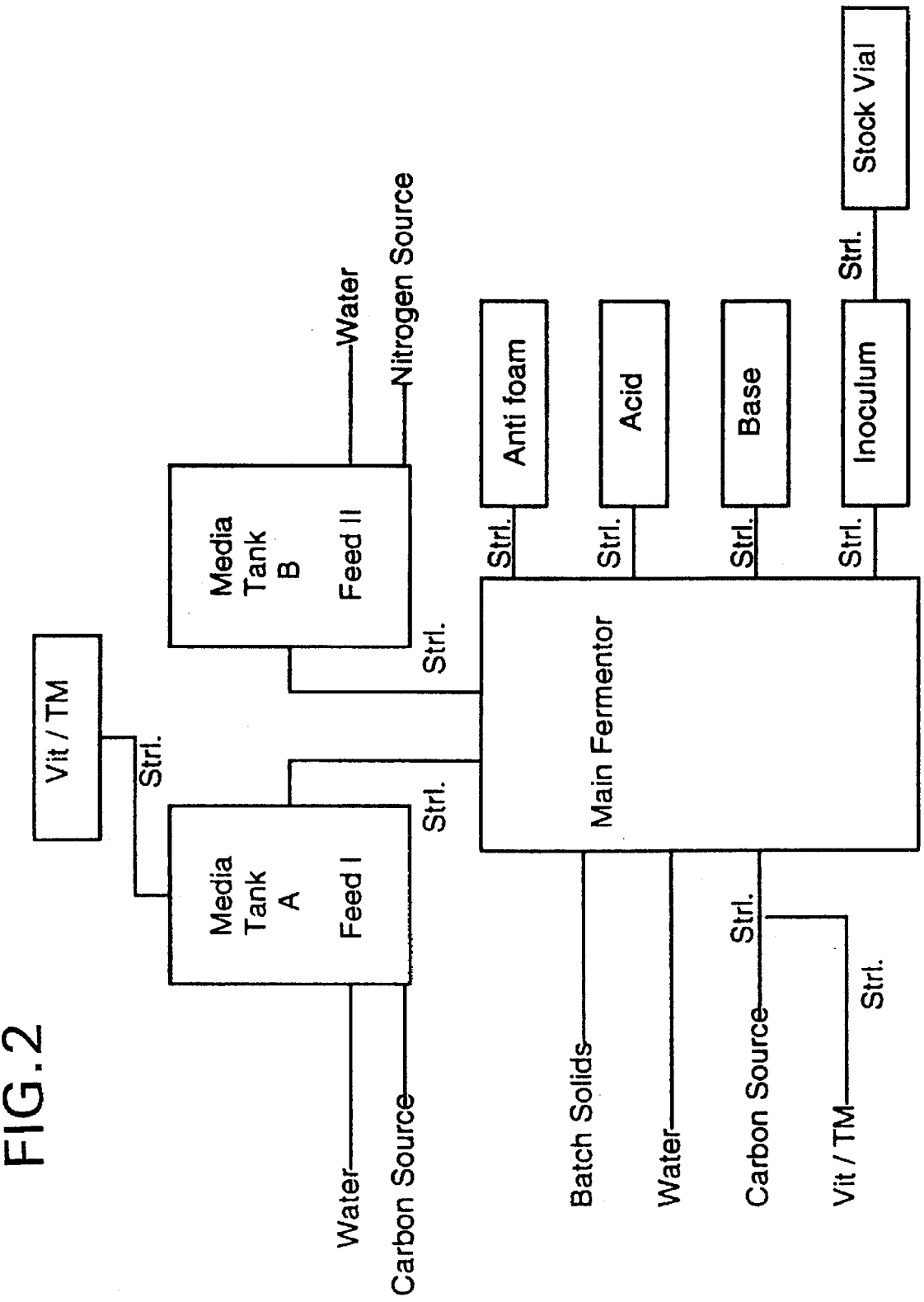
FIG. 2 depicts a fed batch split feed fermentation system of the present invention. Abbreviations are as indicated in FIG. 1.

The procedure employed in this Example to prepare rSCF is readily understood by reference to FIG. 2. This procedure is a simplified method for making rSCF as compared to the procedure set forth in Example 1.

The batch medium used in the fermentor for initial growth of the host cells was prepared by adding about 12.5 g/l of yeast extract (Becton-Dickinson, Cockeysville, Md.), monobasic potassium phosphate and dibasic potassium phosphate, both at about 4.0 g/l, NaCl to about 0.6 g/l, and water to about 5.3 liters into the fermentor. Antifoam (Dow P-2000, Dow Chemical Company) was then added at a concentration of about 1 g/l initially, and then was added subsequently throughout the fermentation process as needed to prevent foaming. This solution was then heat sterilized in situ. A solution of about 40 g glucose in 200 ml distilled water, and a second solution of about 32 ml of a 1M solution of magnesium sulfate ($MgSO_4*7H_2O$) that had been previously sterilized, were both added to the fermentor through a port. Distilled, sterile water was added to the fermentor to bring the final glucose concentration to about 5 g/l, and the final magnesium sulfate concentration to about 4 ml/l. Simultaneously, a solution of vitamins and trace minerals, previously filter sterilized, was added to the fermentor. Acid and base solutions of phosphoric acid and ammonium hydroxide were added as necessary to maintain a pH of about 7.0.

A vial of previously frozen E. coli cells strain K-12 that had been transfected with a plasmid containing the gene encoding human SCF was slowly thawed and added under sterile conditions to an inoculum shaker flask containing about 500 ml LB broth. The flask was kept shaking at about 30° C. After about 8–12 hours (or when the $OD_{600}$ was greater than 1.0), the shaker flask of cells was transferred under sterile conditions to a fermentor. The fermentor was sparged with air and oxygen as needed.

When the $OD_{600}$ in the fermentor reached about 5.0 (indicating that the glucose level was less than about 0.5 g/l), Feed 1, which was attached to the fermentor by silicone tubing, was started. The contents of Feed 1 were prepared as follows.

Glucose at about 700 g/l and about 55 ml/l of 1M $MgSO_4*7H_2O$ were combined and brought to volume with distilled water. This solution was then heat sterilized in the tank (Media Tank A in FIG. 2). After sterilization, filter sterilized solutions of trace minerals and vitamins (as set forth in Example 1) were added. The flow rate of Feed 1 was increased with time, as shown below on Table 4.

TABLE 4

FLOW RATE FOR FEED 1

| TIME (hrs) | VOLUMETRIC FLOW (ml/hr) | MASS FLOW (g Glucose/hr) |
|---|---|---|
| 0.00 | 10.60 | 7.42 |
| 2.00 | 17.60 | 12.32 |
| 4.00 | 29.06 | 20.34 |
| 6.00 | 47.96 | 33.57 |
| 8.00 | 79.07 | 55.35 |
| 9.00 | 101.60 | 71.12 |
| 10.00 | 130.50 | 91.35 |
| 11.11 | 173.60 | 121.52 |

After about 10 hours, or when the $OD_{600}$ reached about 50, the host cells were induced to produce rSCF by increasing the temperature of the fermentor to about 42° C. The rate of flow for Feed 1 was simultaneously decreased to about 50 ml/hour and was kept at that rate through the remainder of the fermentation period, and Feed 2 was started.

Feed 2 was prepared by adding about 258 g/l of Trypticase Peptone, about 129 g/l of yeast extract, and about 6.5 g/l of $K_2HPO_4$ to the tank, and bringing it to volume with distilled water. Feed 2 was pumped into the fermentor at a constant rate of about 175 ml/hour through the remainder of the fermentation period which was about 10 hours. The composition of the medium added to the fermentor during this production phase of fermentation is shown below in Table 5.

TABLE 5

| BACTO TRYPTONE (g/hr) | 45.2 |
|---|---|
| YEAST EXTRACT (g/hr) | 22.6 |
| K2HPO4 (g/hr) | 1.14 |
| GLUCOSE (g/hr) | 35 |
| MGSO4*H2O (ml/hr) | 2.75 |
| TM (ml/hr) | 0.8 |
| VITAMINS (ml/hr) | 0.8 |

As is apparent, the composition of the medium, as well as the concentration of each ingredient was very similar to the production phase medium used in Example 1.

After the fermentation process was terminated by chilling the fermentor to about 10° C, the host cells were collected, the inclusion bodies extracted, and the rSCF was purified. The yield of rSCF, as measured by SDS-polyacrylamide gel electrophoresis from two separate fermentation runs is set forth below in Table 6.

TABLE 6

YIELD OF rSCF

| Run No. | Final $OD_{600}$ | rSCF Yield (g/l) |
|---|---|---|
| 1 | 57 | 1.62 |
| 2 | 68 | 2.07 |
| Average | 62.5 | 1.845 |

We claim:

1. A method for fed batch culturing of cells in a fermentor comprising independently introducing into the fermentor during the growth and production phases of culturing:

a) a carbon nutrient source from a first feed vessel; and b) a nitrogen nutrient source from a second feed vessel.

2. The method of claim 1 wherein the carbon and nitrogen nutrient sources are independently introduced into the fermentor by a rate control means.

3. The rate control means of claim 2 that is a pump.

4. The method of claims 1, 2, or 3 wherein the cells are bacteria cells.

5. A method for preparing a compound of interest comprising fed batch culturing of host cells that produce the compound wherein a carbon nutrient source is introduced to the fermentor from a first feed vessel and a nitrogen nutrient source is introduced to the fermentor form a second feed vessel, and wherein the nutrient sources are delivered to the fermentor at independent rates during both the growth and production phases of culturing.

6. The method of claim 5 wherein the carbon and nitrogen nutrient sources are independently introduced to the fermentor by a rate control means.

7. The method of claim 5 wherein the rate control means is a pump.

\* \* \* \* \*

UNITED STATES PATENT AND TRADEMARK OFFICE
CERTIFICATE OF CORRECTION

PATENT NO.    : 5,639,658

DATED         : June 17, 1997

INVENTOR(S)   : Drobish *et al.*

It is certified that error appears in the above-identified patent and that said Letters Patent is hereby corrected as shown below:

Title Page: Item [56] Column 1, References Cited, Foreign Patent Documents, Line 1, change "290215 A5" to --290212 A5--.

Column 5, line 19, change "compound" to --producing--.

Column 14, line 34, add a comma after the word, "compound".

Column 14, line 36, change "form" to --from--.

Signed and Sealed this

Seventh Day of April, 1998

*Attest:*

BRUCE LEHMAN

*Attesting Officer*    Commissioner of Patents and Trademarks